United States Patent
Sakanishi et al.

(10) Patent No.: US 11,104,638 B2
(45) Date of Patent: Aug. 31, 2021

(54) THICKENING STABILIZER

(71) Applicants: DAICEL CORPORATION, Osaka (JP); YAMAGUCHI UNIVERSITY, Yamaguchi (JP)

(72) Inventors: Yuichi Sakanishi, Tokyo (JP); Takashi Saeki, Ube (JP); Aya Kaide, Ube (JP)

(73) Assignees: DAICEL CORPORATION, Osaka (JP); YAMAGUCHI UNIVERSITY, Yamaguchi (JP)

( * ) Notice: Subject to any disclaimer, the term of this patent is extended or adjusted under 35 U.S.C. 154(b) by 262 days.

(21) Appl. No.: 16/327,283

(22) PCT Filed: Jul. 20, 2017

(86) PCT No.: PCT/JP2017/026303
§ 371 (c)(1),
(2) Date: Feb. 21, 2019

(87) PCT Pub. No.: WO2018/042933
PCT Pub. Date: Mar. 8, 2018

(65) Prior Publication Data
US 2020/0216385 A1    Jul. 9, 2020

(30) Foreign Application Priority Data
Aug. 29, 2016  (JP) .............................. JP2016-166636

(51) Int. Cl.
*A61K 9/00*      (2006.01)
*A61K 47/00*     (2006.01)
*C07C 233/65*    (2006.01)
*A61K 8/42*      (2006.01)
*A61K 47/18*     (2017.01)

(52) U.S. Cl.
CPC .............. *C07C 233/65* (2013.01); *A61K 8/42* (2013.01); *A61K 47/18* (2013.01); *A61K 2800/48* (2013.01)

(58) Field of Classification Search
CPC ....... A61K 47/18; A61K 2800/48; A61K 8/42
USPC .......................... 514/788, 616, 617; 424/400
See application file for complete search history.

(56) References Cited

U.S. PATENT DOCUMENTS

2013/0085087 A1\* 4/2013 Mesher ................... C09K 8/035
                                                          507/131
2015/0376119 A1   12/2015 Sakanishi et al.

FOREIGN PATENT DOCUMENTS

JP            1-163111 A        6/1989

OTHER PUBLICATIONS

Extended European Search Report dated Mar. 17, 2020, in European Patent Application No. 17845943.4.
Sakanishi et al., "Development of New Series of Organogelators: N,N',N",N'''-1,2,4,5,-tetra alkyl/alkenyl pyromellitamides," Journal of the Society of Rheology (Feb. 23, 2015), vol. 43, No. 1, pp. 1-9.
International Search Report dated Aug. 22, 2017, in PCT/JP2017/026303, with English translation.
Written Opinion of the International Searching Authority dated Aug. 22, 2017, in PCT/JP2017/026303, with English translation.
Office Action dated Dec. 31, 2020, in Taiwan Patent Application No. 106129095.

\* cited by examiner

*Primary Examiner* — Shengjun Wang
(74) *Attorney, Agent, or Firm* — Birch, Stewart, Kolasch & Birch, LLP

(57) ABSTRACT

Provided is a thickening/stabilizing agent that thickens, gelatinizes, and/or stabilizes a fluid organic substance to a desired viscosity. The thickening/stabilizing agent according to the present invention contains a compound (1) represented by Formula (i) and a compound (2) represented by Formula (ii), in a mole ratio of the compound (1) to the compound (2) of 95:5 to 25:75. The four $R^1$s in Formula (i) represent, identically in each occurrence, a $C_{12}$-$C_{18}$ aliphatic hydrocarbon group; and the four $R^2$s in Formula (ii) represent, identically in each occurrence, an $C_4$-$C_{10}$ aliphatic hydrocarbon group. Formulae (i) and (ii) are expressed as follows:

[Chem. 1]

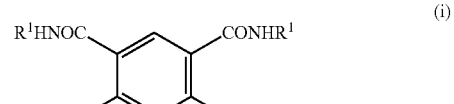

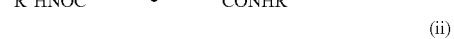

4 Claims, No Drawings

THICKENING STABILIZER

TECHNICAL FIELD

The present invention relates to a novel thickening/stabilizing agent that thickens and/or stabilizes oils and other fluid organic substances; and a thickened/stabilized composition containing the thickening/stabilizing agent. This application claims priority to Japanese Patent Application No. 2016-166636, filed to Japan on Aug. 29, 2016, the entire contents of which are incorporated herein by reference.

BACKGROUND ART

Techniques for thickening/stabilizing liquids are industrially very important. For example, mayonnaise and salad dressing, which are emulsions in a metastable state, can stably maintain their emulsified state over the long term, because of thickening/stabilization of an aqueous component or components therein. For such thickening/stabilization, various thickening/stabilizing agents have been developed.

For example, 12-hydroxystearic acid is known as a thickening/stabilizing agent for fluid organic substances (e.g., Patent Literature (PTL) 1), where the fluid organic substances are exemplified by oily media and other organic substances having fluidity. Utilizing its gelatinizing activity, 12-hydroxystearic acid is mainly used for waste disposal of edible oils. However, 12-hydroxystearic acid is unadjustable in degree of gelatinization, and the target component can only be brought into a completely solidified state or remain in a liquid state as intact. Namely, under present circumstances, there has not yet been found a compound that thickens or gelatinizes a fluid organic substance to a desired viscosity.

CITATION LIST

Patent Literature

PTL 1: Japanese Unexamined Patent Application Publication (JP-A) No. H01-163111

SUMMARY OF INVENTION

Technical Problem

Accordingly, the present invention has an object to provide a thickening/stabilizing agent that thickens, gelatinizes, and/or stabilizes a fluid organic substance to a desired viscosity.

The present invention has another object to provide a thickened/stabilized composition including a fluid organic substance that is thickened, gelatinized, and/or stabilized by the thickening/stabilizing agent, and a method for producing the thickened/stabilized composition.

Solution to Problem

After intensive investigations to achieve the objects, the inventors of the present invention found that two different compounds each corresponding to 1,2,4,5-benzenetetracarboxamide and containing Rs in [—CONHR]groups being an aliphatic hydrocarbon group containing a specific number of carbon atoms, fail to give sufficient thickening/stabilizing effects when each used alone; but that a composition containing both the two compounds in combination in a specific ratio can offer excellent thickening/stabilizing effects on a wide variety of fluid organic substances. More specifically, the thickening/stabilizing effects are thickening, gelatinizing, and/or stabilizing effects, where the stabilizing effects are the effects of: eliminating or minimizing sedimentation, local aggregation, and concentrating of a composition containing a fluid organic substance; and allowing the composition to stably maintain its uniform state. The present invention has been made on the basis of these findings.

Specifically, the present invention provides, in one aspect, a thickening/stabilizing agent containing a compound (1) represented by Formula (i) and a compound (2) represented by Formula (ii), in a mole ratio of the compound (1) to the compound (2) of 95:5 to 25:75. Formulae (i) and (ii) are expressed as follows:

[Chem. 1]

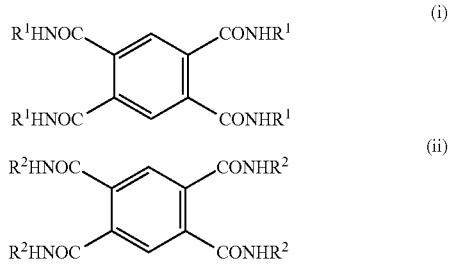

wherein the four $R^1$s in Formula (i) represent, identically in each occurrence, an $C_{12}$-$C_{18}$ aliphatic hydrocarbon group; and the four $R^2$s in Formula (ii) represent, identically in each occurrence, an $C_4$-$C_{10}$ aliphatic hydrocarbon group.

In the thickening/stabilizing agent, it is preferred that the $R^1$s in Formula (i) represent, identically in each occurrence, a $C_{12}$-$C_{18}$ linear unsaturated aliphatic hydrocarbon group; and the $R^2$s in Formula (ii) represent, identically in each occurrence, a $C_4$-$C_{10}$ branched chain saturated aliphatic hydrocarbon group.

The present invention also provides, in another aspect, a thickened/stabilized composition including the thickening/stabilizing agent and a fluid organic substance.

The present invention provides, in yet another aspect, a method for producing a thickened/stabilized composition. The method includes the step of dissolving the thickening/stabilizing agent and a fluid organic substance mutually in each other.

Advantageous Effects of Invention

The thickening/stabilizing agent according to the present invention can offer excellent thickening/stabilizing effects on a wide variety of fluid organic substances. More specifically, the thickening/stabilizing agent according to the present invention, when dissolved mutually in a fluid organic substance, can adjust the viscosity of the fluid organic substance within a desired range, and allows the resulting composition containing the fluid organic substance to maintain its chemical composition uniformly. This contributes to better usability of the composition containing the fluid organic substance. The thickened/stabilized composition, which is thickened/stabilized using the thickening/stabilizing agent according to the present invention, has appropriate viscosity and elasticity and offers secure thickness. Accordingly, the thickening/stabilizing agent according to the present invention is advantageously useable in the fields that require thickening/stabilizing of fluid organic substances, such as the fields of cosmetics, coating materials, foodstuffs, and pharmaceutical preparations.

DESCRIPTION OF EMBODIMENTS

Thickening/Stabilizing Agent

The thickening/stabilizing agent according to the present invention includes a compound (1) represented by Formula (i) and a compound (2) represented by Formula (ii), in a mole ratio of the compound (1) to the compound (2) of 95:5 to 25:75, where Formulae (i) and (ii) are expressed as follows:

[Chem. 2]

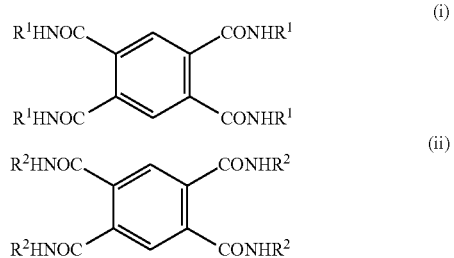

wherein the four $R^1$s in Formula (i) represent, identically in each occurrence, an $C_{12}$-$C_{18}$ aliphatic hydrocarbon group; and the four $R^2$s in Formula (ii) represent, identically in each occurrence, an $0_4$-$C_{10}$ aliphatic hydrocarbon group.

As used herein, the term "thickening/stabilizing agent" refers to a compound that is dissolved in a fluid organic substance to give viscosity; and is a concept that includes thickeners which impart viscosity to the fluid organic substance; gelling agents which gelatinize the fluid organic substance; and stabilizers which allow a composition containing the fluid organic substance to have a uniformly stabilized chemical composition.

In Formula (i), $R^1$s are each identically an $C_{12}$-$C_{18}$ aliphatic hydrocarbon group. The aliphatic hydrocarbon group herein includes linear or branched chain saturated aliphatic hydrocarbon groups and linear or branched chain unsaturated aliphatic hydrocarbon groups. Non-limiting examples of $R^1$s include linear or branched alkyls such as lauryl, myristyl, and stearyl; linear or branched alkenyls such as 11-dodecenyl and oleyl; and linear or branched alkynyls such as pentadecynyl and octadecynyl.

Among them, $R^1$s are preferably selected from $C_{12}$-$C_{18}$ (in particular $C_{14}$-$C_{18}$) linear or branched chain unsaturated aliphatic hydrocarbon groups, particularly preferably selected from linear unsaturated aliphatic hydrocarbon groups, and most preferably selected from linear alkenyls such as oleyl.

In Formula (ii), $R^2$s are each identically an $C_4$-$C_{10}$ aliphatic hydrocarbon group. The aliphatic hydrocarbon group herein includes linear or branched chain saturated aliphatic hydrocarbon groups and linear or branched chain unsaturated aliphatic hydrocarbon groups. Non-limiting examples of $R^2$s include linear or branched alkyls such as butyl, hexyl, octyl, 2-ethylhexyl, and decyl; linear or branched alkenyls such as 2-hexenyl, 3-hexenyl, 4-hexenyl, 5-hexenyl, 7-octenyl, and 9-decenyl; and linear or branched alkynyls such as hexynyl, octynyl, and decynyl.

Among them, $R^2$s are preferably selected from $C_4$-$C_{10}$ (in particular, $C_6$-$C_{10}$) linear or branched chain saturated aliphatic hydrocarbon groups, particularly preferably selected from branched chain saturated aliphatic hydrocarbon groups, and most preferably selected from branched alkyls such as 2-ethylhexyl.

The compound (1) and the compound (2) can be produced typically by one of the following methods 1 and 2.

In the method 1, pyromellitic acid (i.e., 1,2,4,5-benzenetetracarboxylic acid) is reacted with thionyl chloride to give pyromellitic acid tetrachloride, and the pyromellitic acid tetrachloride is reacted with an alkylamine (1) ($R^2$—$NH_2$) or an alkylamine (2) ($R^2$—$NH_2$), where $R^1$ and $R^2$ are as defined above.

In the method 2, pyromellitic acid is esterified to give a pyromellitic acid ester, and the pyromellitic acid ester is reacted with an alkylamine (1) ($R^1$—$NH_2$) or an alkylamine (2) ($R^2$—$NH_2$), where $R^1$ and $R^2$ are as defined above.

In particular, the production method 1 is preferably employed in the present invention, for high product purity.

Non-limiting examples of the alkylamine (R'—$NH_2$) include laurylamine, myristylamine, stearylamine, oleylamine, and other amines containing a $C_{12}$-$C_{18}$ (preferably $C_{14}$-$C_{18}$) aliphatic hydrocarbon group (of which a linear or branched alkyl, alkenyl, or alkynyl is preferred).

Non-limiting examples of the alkylamine ($R^2$—$NH_2$) include amines containing a $C_4$-$C_{10}$ (preferably $C_6$-$C_{10}$) aliphatic hydrocarbon group such as butyl, hexyl, octyl, 2-ethylhexyl, or decyl (of which a linear or branched alkyl, alkenyl, or alkynyl is preferred).

In the production method 1, the reaction between pyromellitic acid tetrachloride and the alkylamine may be performed typically by adding pyromellitic acid tetrachloride dropwise to a system including the alkylamine.

The alkylamine (the alkylamine (1) or the alkylamine (2)) is used in an amount of typically about 4 to about 8 moles, and preferably 4 to 6 moles, per mole of pyromellitic acid tetrachloride.

The reaction between pyromellitic acid tetrachloride and the alkylamine may be performed in the presence of, or in the absence of, a solvent. Non-limiting examples of the solvent include saturated or unsaturated aliphatic hydrocarbon solvents such as pentane, hexane, heptane, octane, and petroleum ether; aromatic hydrocarbon solvents such as benzene, toluene, and xylenes; halogenated hydrocarbon solvents such as methylene chloride, chloroform, 1,2-dichloroethane, chlorobenzene, and bromobenzene; ether solvents such as diethyl ether, diisopropyl ether, dibutyl ether, tetrahydrofuran, dioxane, 1,2-dimethoxyethane, and cyclopentyl methyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oils. Each of them may be used alone or in combination.

The solvent is used in an amount of typically about 50 to about 300 weight percent, relative to the totality of pyromellitic acid tetrachloride and the alkylamine. The solvent, if used in an amount greater than the range, tends to cause a lower reaction rate, because of lower concentrations of the reaction components.

The reaction (i.e., dropwise addition) of pyromellitic acid tetrachloride with (to) the alkylamine is generally performed at normal atmospheric pressure. The atmosphere in the reaction (i.e., dropwise addition) is not limited, as long as adversely affecting the reaction, and may be any atmosphere such as air atmosphere, nitrogen atmosphere, or argon atmosphere. The reaction temperature (i.e., dropwise addition temperature) is typically about 30° C. to about 60° C.

The reaction time (i.e., dropwise addition time) is typically about 0.5 to about 20 hours. The method may include an aging step after the completion of the reaction (i.e., dropwise addition). When the aging step is provided, the aging may be performed at a temperature of typically about 30° C. to 60° C. for a time of typically about 1 to about 5 hours. The reaction may be performed by any system such as a batch system, semi-batch system, or continuous system.

After the completion of the reaction, the resulting reaction product can be separated and purified by a separation means such as filtration, concentration, distillation, extraction, crystallization, adsorption, recrystallization, or column chromatography, or a separation means as any combination of them.

The compound (1) and the compound (2) can undergo self-association by hydrogen bonding at amide bond sites to form a fibrous self-assembled structure. Since the groups $R^1$ and $R^2$ in Formula (i) and Formula (ii) have affinity for a fluid organic substance, the compounds (1) and (2) can thicken, gelatinize, and/or stabilize the fluid organic substance, by dissolving the compounds and the fluid organic substance mutually in each other. In addition, a composition containing both the compound (1) and the compound (2) has appropriate crystallinity (crystal plasticity). This configuration enables thickening or stabilization of any organic substance having fluidity without limitation. When the fluid organic substance has transparency, the configuration enables thickening/stabilization of the fluid organic substance while maintaining the transparency and can give a thickened/stabilized composition that is stable with time. The compounds in combination are therefore useful typically as or for thickening/stabilizing agents for fluid organic substances. Specifically, the compounds in combination are useful as or for any of thickeners, gelling agents, and stabilizers for fluid organic substances.

The thickening/stabilizing agent according to the present invention contains the compound (1) and the compound (2) in a mole ratio of the compound (1) to the compound (2) of from 95:5 to 25:75. The blending ratio (mole ratio) of the compound (1) to the compound (2) is more preferably from 90:10 to 30:70, particularly preferably from 85:15 to 40:60, and most preferably from 80:20 to 45:55. The compound (1) has high solubility in (or high solving power for) fluid organic substances. The thickening/stabilizing agent, if containing the compound (1) in a blending ratio greater than the range, tends to offer lower thickening ability. The thickening/stabilizing agent, if containing the compound (1) in a blending ratio less than the range, tends to be limited in fluid organic substances which the agent can thicken and/or stabilize, because of having excessively high crystallinity. This thickening/stabilizing agent may often become cloudy as a result of thickening/stabilization and tends to have a poor appearance. In addition, this thickening/stabilizing agent tends to have a decreasing viscosity with time.

The thickening/stabilizing agent according to the present invention may further contain one or more other components as needed, in addition to the compound (1) and the compound (2). Non-limiting examples of such other components include vehicles, hydroxyfatty acids, acrylic polymers, dextrin fatty acid esters and other oligomer esters, and particles typically of metal oxides. The other component(s) may be present in a content within such a range that the total content of the compound (1) and the compound (2) is typically 0.5 weight percent or more, preferably 1 weight percent or more, more preferably 10 weight percent or more, particularly preferably 30 weight percent or more, and most preferably 60 weight percent or more, of the totality (100 weight percent) of the thickening/stabilizing agent. The upper limit of the total content of the compound (1) and the compound (2) is 100 weight percent. The thickening/stabilizing agent, if containing the compound (1) and the compound (2) in a total content less than the range, tends to hardly offer advantageous effects of the present invention.

The thickening/stabilizing agent according to the present invention may employ any of various forms (formulations) such as forms of powders, granules, liquids, and milky lotions.

Assume that the thickening/stabilizing agent according to the present invention and a fluid organic substance are dissolved mutually in each other (preferably, the thickening/stabilizing agent is mixed with the fluid organic substance and heated to dissolve them in each other, and the resulting mixture is cooled). The thickening/stabilizing agent in this case can thicken and/or gelatinize the fluid organic substance and can control the viscosity of the fluid organic substance according to the intended use, within the range of typically from greater than 1 time to about 600 times.

Thickened/Stabilized Composition

The thickened/stabilized composition according to the present invention is a composition including the thickening/stabilizing agent and a fluid organic substance, in which the fluid organic substance is thickened, gelatinized, and/or stabilized by the action of the thickening/stabilizing agent.

The thickened/stabilized composition can be produced through the step of dissolving the thickening/stabilizing agent and the fluid organic substance mutually in each other. More specifically, the thickened/stabilized composition may be produced by mixing the thickening/stabilizing agent with the whole quantity of the fluid organic substance, and heating the mixture to dissolve the two components mutually in each other, followed by cooling. The thickened/stabilized composition may also be produced by mixing the thickening/stabilizing agent with a portion of the fluid organic substance, heating the mixture to dissolve them mutually in each other, cooling the mixture to give a thickened/stabilized composition, and mixing the composition with the remainder of the fluid organic substance.

Upon mutual dissolution of the thickening/stabilizing agent and the fluid organic substance, the compound (1) and the compound (2) constituting the thickening/stabilizing agent may be mixed with each other before the addition to the fluid organic substance, or may be separately added to the fluid organic substance and mixed with each other in the fluid organic substance.

The fluid organic substance, which serves as a raw material, is an organic substance having a viscosity of typically less than 0.1 Pa·s, where the viscosity is measured using a rheometer and is a viscosity ($\eta$) at a temperature of 25° C. and a shear rate of 10 ($s^{-1}$). Non-limiting examples of the fluid organic substance include hydrocarbon oils such as hexane, cyclohexane, isododecane, benzene, toluene, poly-α-olefins, and liquid paraffin; ethers such as tetrahydrofuran; halogenated hydrocarbons such as carbon tetrachloride and chlorobenzene; petroleum components such as kerosene, gasoline, light oils, and heavy oils; animal and vegetable oils such as sunflower oil, olive oil, soybean oil, corn oil, castor oil, beef tallow, jojoba oil, and squalane; silicones such as dimethylpolysiloxanes and methylphenylpolysiloxanes; esters such as octyldodecyl oleate, cetyl octanoate, cetyl ethylhexanoate, glyceryl triisooctanoate, and neopentyl glycol diisooctanoate; aromatic carboxylic acids; and pyridine. The composition may include each of them alone or in combination.

The amount of the thickening/stabilizing agent to be mixed (or to be used) is typically 0.1 to 100 parts by weight, preferably 0.5 to 90 parts by weight, and particularly preferably 1 to 80 parts by weight, per 1000 parts by weight of the fluid organic substance, while the amount may vary depending on the type of the fluid organic substance.

In addition to the thickening/stabilizing agent and the fluid organic substance, the thickened/stabilized composition according to the present invention may further contain one or more other components within ranges not adversely affecting the advantageous effects of the present invention. Non-limiting examples of such other components include medicinal components, pigments, flavors, and any other regular components to be contained in cosmetics, coating materials, foodstuffs, pharmaceuticals, and any other compositions that require thickening/stabilization.

The temperature upon mutual dissolution may be selected as appropriate according to the types of the thickening/stabilizing agent and the fluid organic substance to be used, and is not limited as long as being such a temperature that the thickening/stabilizing agent and the fluid organic substance are dissolved in each other. The temperature is, however, preferably not higher than 100° C. When the fluid organic substance has a boiling point of 100° C. or lower, the temperature is preferably around the boiling point.

The cooling after the mutual dissolution (blending) has only to be performed so that the resulting composition can be cooled down to 25° C. or lower. The cooling may be gradual cooling at room temperature, or rapid cooling typically by ice cooling.

The viscosity of the thickened/stabilized composition according to the present invention can be controlled as appropriate according to the intended use, within the range of from greater than 1 time to 600 times as much as the viscosity of the raw material fluid organic substance, where the viscosity is measured using a rheometer and is a viscosity ($\eta$) at a temperature of 25° C. and a shear rate of 10 ($s^{-1}$).

The thickened/stabilized composition according to the present invention is not limited, as long as being a composition containing a fluid organic substance and desiring to be thickened/stabilized. Non-limiting examples of the thickened/stabilized composition include cosmetics, coating materials, foodstuffs, and pharmaceuticals.

EXAMPLES

The present invention will be illustrated in further detail with reference to several examples below. It should be noted, however, that the examples are by no means intended to limit the scope of the present invention.

Synthetic Example 1

Synthesis of Compound (I)
(1,2,4,5-benzenetetracarboxylic acid tetraoleylamide)

Into a 100-mL four-necked separable flask equipped with a Dimroth condenser, a nitrogen inlet, a dropping funnel, and a thermocouple, 20 mL of chloroform and 9.8 g (0.036 mol) of oleylamine were charged. The system internal temperature was set to 40° C.

Thereafter 10 mL of a chloroform solution containing 3 g (0.009 mol) of pyromellitic acid tetrachloride was added dropwise over 2 hours, followed by aging for further 2 hours.

A crude reaction mixture was then obtained, from which low-boiling components were removed using an evaporator, the residue was washed with methanol, and yielded a white wet powder. The wet powder was further recrystallized from $CHCl_3/CH_3OH$ (70/30 (v/v)) and yielded 6.4 g of 1,2,4,5-benzenetetracarboxylic acid tetraoleylamide (in a yield of 56%). The structure of the reaction product was identified by $^1$H-NMR.

$^1$H-NMR (270 MHz, $CDCl_3$): δ 0.81-0.95 (m, 12H), 1.03-1.85 (m, 88H), 1.96-2.04 (m, 8H), 3.12-3.40 (m, 4H), 5.35-5.56 (m, 8H), 8.7-9.1 (m, 2H)

Synthetic Example 2

Synthesis of Compound (II)
(1,2,4,5-benzenetetracarboxylic acid tetra(2-ethylhexylamide))

A procedure similar to that in Synthetic Example 1 was performed, except for using 4.8 g (0.036 mol) of 2-ethylhexylamine instead of oleylamine. This gave 3.7 g of 1,2,4,5-benzenetetracarboxylic acid tetra(2-ethylhexylamide) (in a yield of 59%). The structure of the reaction product was identified by $^1$H-NMR.

$^1$H-NMR (270 MHz, $CDCl_3$): δ 0.81-1.01 (m, 24H), 1.21-1.83 (m, 40H), 3.25-3.40 (m, 4H), 8.5-9.5 (m, 2H)

Examples 1 and 2, and Comparative Examples 1 and 2

Each of the fluid organic substances listed in Table 1 was weighed in a volume of 1 $cm^3$ in a test tube, and combined with the compound (I) and/or the compound (II) obtained in the synthetic examples. The mixture was stirred with heating at 100° C. to dissolve the components mutually, and was cooled down to 25° C. Thus, a series of compositions was obtained.

The viscosities of the prepared thickened/stabilized compositions were measured, how many times the viscosities of the fluid organic substances were increased was determined, and the thickening ability was evaluated according to criteria as follows.

Criteria

Failure: not dissolved
1: from greater than 1.0 time to 2.0 times
2: from greater than 2.0 times to 4.8 times
3: from greater than 4.8 times to 10 times
4: from greater than 10 times to 50 times
5: from greater than 50 times to 100 times
6: greater than 100 times The viscosities of the fluid organic substances and the compositions were measured and determined in the following manner. The viscosity measurement employed a viscosity/visco-elastometer (rheometer) (HAAKE RheoStress 600 (trade name)) equipped with a cone-and-plate sensor and a Peltier temperature controller. The cone-and-plate system in the sensor had a diameter of 60 mm with a cone angle of 1°, or a diameter of 35 mm with a cone angle of 1°, 2°, or 4°. The viscosities were measured in a steady flow viscosity measurement mode at 25° C. and at different shear rates varying in a log scale from 0.001 to 100 ($s^{-1}$), based on which a viscosity curve was plotted. A viscosity at a shear rate of 10 ($s^{-1}$) was determined on the basis of the viscosity curve, and this was defined as the viscosity in the present invention. Each plot employed values obtained at the time point when the torque value variation of the instrument was settled within the range of 5% and the data became stable.

The results are collectively given in the table below.

TABLE 1

| | | Example 1 | Example 2 | Comparative Example 1 | Comparative Example 2 |
|---|---|---|---|---|---|
| Thickening/stabilizing agent | Compound (I) (mole ratio) | 50 | 75 | — | 100 |
| | Compound (II) (mole ratio) | 50 | 25 | 100 | — |
| Thickening ability on fluid organic substance | Liquid paraffin | 5 | 3 | Failure | 3 |
| | Isododecane | 6 | 4 | Failure | 4 |
| | Cetyl octanoate | 6 | 4 | Failure | 3 |

The results of Examples 1 and 2 demonstrate that the compositions prepared using the thickening/stabilizing agents according to the present invention, which contain both the compound (I) and the compound (II), had viscosity and appropriate elasticity. Namely, the compositions had secure thickness. In contrast, the results of Comparative Example 1 demonstrate that the compound (II), when used alone, failed to impart viscosity and elasticity to the fluid organic substances. The results of Comparative Example 2 demonstrate that the composition prepared using the compound (I) alone had viscosity at a comparable level, but had lower elasticity, as compared with Example 2. Specifically, the results demonstrate that the compound (I), when used alone, fails to impart secure thickness to the fluid organic substances.

As a summary of the above description, configurations according to embodiments of the present invention, as well as variations thereof, will be listed below as appendices.

(1) A thickening/stabilizing agent including a compound (1) represented by Formula (i) and a compound (2) represented by Formula (ii), in a mole ratio of the compound (1) to the compound (2) of 95:5 to 25:75, wherein the four $R^1$s in Formula (i) represent, identically in each occurrence, an $C_{12}$-$C_{18}$ aliphatic hydrocarbon group; and the four $R^2$s in Formula (ii) represent, identically in each occurrence, an $C_4$-$C_{10}$ aliphatic hydrocarbon group.

(2) The thickening/stabilizing agent according to (1), wherein $R^1$s in Formula (i) are, identically in each occurrence, a $C_{12}$-$C_{18}$ linear or branched chain unsaturated aliphatic hydrocarbon group, a $C_{14}$-$C_{18}$ linear or branched chain unsaturated aliphatic hydrocarbon group, a $C_{12}$-$C_{18}$ linear unsaturated aliphatic hydrocarbon group, a $C_{14}$-$C_{18}$ linear unsaturated aliphatic hydrocarbon group, or a linear alkenyl such as oleyl.

(3) The thickening/stabilizing agent according to one of (1) and (2), wherein $R^2$s in Formula (ii) are, identically in each occurrence, a $C_4$-$C_{10}$ linear or branched chain saturated aliphatic hydrocarbon group, a $C_6$-$C_{10}$ linear or branched chain saturated aliphatic hydrocarbon group, a $C_4$-$C_{10}$ branched chain saturated aliphatic hydrocarbon group, a $C_6$-$C_{10}$ branched chain saturated aliphatic hydrocarbon group, or a branched alkyl such as 2-ethylhexyl.

(4) The thickening/stabilizing agent according to any one of (1) to (3), wherein $R^1$s in Formula (i) represent, identically in each occurrence, a $C_{12}$-$C_{18}$ linear unsaturated aliphatic hydrocarbon group, and wherein $R^2$s in Formula (ii) represent, identically in each occurrence, a $C_4$-$C_{10}$ branched chain saturated aliphatic hydrocarbon group.

(5) The thickening/stabilizing agent according to any one of (1) to (4), wherein the compound (1) and the compound (2) are present in a ratio (mole ratio) of the compound (1) to the compound (2) of from 90:10 to 30:70, from 85:15 to 40:60, or from 80:20 to 45:55.

(6) A thickened/stabilized composition including a fluid organic substance and the thickening/stabilizing agent according to any one of (1) to (5).

(7) The thickened/stabilized composition according to (6), wherein the fluid organic substance is an organic substance having a viscosity of less than 0.1 Pa·s, where the viscosity is measured using a rheometer and is a viscosity ($\eta$) at a temperature of 25° C. and a shear rate of 10 ($s^{-1}$).

(8) The thickened/stabilized composition according to one of (6) and (7), wherein the fluid organic substance is at least one selected from the group consisting of hydrocarbon oils (such as hexane, cyclohexane, isododecane, benzene, toluene, poly-α-olefins, and liquid paraffin), ethers (such as tetrahydrofuran), halogenated hydrocarbons (such as carbon tetrachloride and chlorobenzene), petroleum components (such as kerosene, gasoline, light oils, and heavy oils), animal and vegetable oils (such as sunflower oil, olive oil, soybean oil, corn oil, castor oil, beef tallow, jojoba oil, and squalane), silicones (such as dimethylpolysiloxanes and methylphenylpolysiloxanes), esters (such as octyldodecyl oleate, cetyl octanoate, cetyl ethylhexanoate, glyceryl triisooctanoate, and neopentyl glycol diisooctanoate), aromatic carboxylic acids, and pyridine.

(9) The thickened/stabilized composition according to any one of (6) to (8), wherein the thickening/stabilizing agent is present in an amount of 0.1 to 100 parts by weight, 0.5 to 90 parts by weight, or 1 to 80 parts by weight, per 1000 parts by weight of the fluid organic substance.

(10) A method for producing a thickened/stabilized composition, the method including the step of mutually dissolving a fluid organic substance and the thickening/stabilizing agent according to any one of (1) to (5) in each other.

INDUSTRIAL APPLICABILITY

The thickening/stabilizing agent according to the present invention can offer excellent thickening/stabilizing effects on a wide variety of fluid organic substances. More specifically, the thickening/stabilizing agent according to the present invention, when dissolved mutually in a fluid organic substance, can control the viscosity of the fluid organic substance within a desired range, and allows the resulting composition including the fluid organic substance to maintain its chemical composition uniformly. Accordingly, the thickening/stabilizing agent can contribute to better usability of the composition including the fluid organic substance. The thickened/stabilized composition, which is thickened/stabilized using the thickening/stabilizing agent according to the present invention, has appropriate viscosity and elasticity and offers secure thickness. The thickening/stabilizing agent according to the present invention is therefore advantageously usable or applicable in the fields that require thickening/stabilizing of fluid organic substances, such as the fields of cosmetics, coating materials, foodstuffs, and pharmaceutical preparations.

The invention claimed is:
1. A thickening/stabilizing agent comprising:
a compound (1) represented by Formula (i); and
a compound (2) represented by Formula (ii),
in a mole ratio of the compound (1) to the compound (2) of 50:50 to 25:75, Formulae (i) and (ii) expressed as follows:

[Chem. 1]

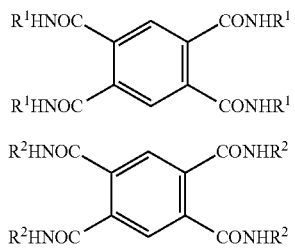

wherein four $R^1$s in Formula (i) represent, identically in each occurrence, an $C_{12}$-$C_{18}$ aliphatic hydrocarbon group; and four $R^2$s in Formula (ii) represent, identically in each occurrence, an $C_4$-$C_{10}$ aliphatic hydrocarbon group.

2. The thickening/stabilizing agent according to claim 1, wherein $R^1$s in Formula (i) represent, identically in each occurrence, a $C_{12}$-$C_{18}$ linear unsaturated aliphatic hydrocarbon group; and $R^2$s in Formula (ii) represent, identically in each occurrence, a $C_4$-$C_{10}$ branched chain saturated aliphatic hydrocarbon group.

3. A thickened/stabilized composition comprising:
the thickening/stabilizing agent according to one of claims 1 and 2; and
a fluid organic substance.

4. A method for producing a thickened/stabilized composition, the method comprising the step of dissolving a fluid organic substance and the thickening/stabilizing agent according to one of claims 1 and 2 mutually in each other.

* * * * *